United States Patent
Griffith et al.

(10) Patent No.: US 11,707,477 B2
(45) Date of Patent: Jul. 25, 2023

(54) FORMULATION COMPRISING A GEMCITABINE-PRODRUG

(71) Applicant: NuCana plc, Edinburgh (GB)

(72) Inventors: Hugh Griffith, Edinburgh (GB); Gordon Kennovin, Edinburgh (GB)

(73) Assignee: NuCana plc, Edinburgh (GB)

( * ) Notice: Subject to any disclaimer, the term of this patent is extended or adjusted under 35 U.S.C. 154(b) by 0 days.

(21) Appl. No.: 17/324,835

(22) Filed: May 19, 2021

(65) Prior Publication Data

US 2022/0031727 A1 Feb. 3, 2022

Related U.S. Application Data

(63) Continuation of application No. 17/010,338, filed on Sep. 2, 2020, now Pat. No. 11,040,051, which is a continuation of application No. 16/142,948, filed on Sep. 26, 2018, now Pat. No. 10,786,523, which is a continuation of application No. 15/308,475, filed as application No. PCT/GB2015/051858 on Jun. 25, 2015, now Pat. No. 10,117,888.

(30) Foreign Application Priority Data

Jun. 25, 2014 (GB) .................................. 1411253
Jun. 25, 2014 (IN) ......................... 2050/MUM/2014
Oct. 6, 2014 (GB) .................................. 1417646

(51) Int. Cl.
| | | |
|---|---|---|
| *A61K 31/7068* | (2006.01) | |
| *A61K 47/16* | (2006.01) | |
| *A61K 9/00* | (2006.01) | |
| *A61K 47/20* | (2006.01) | |
| *A61K 47/22* | (2006.01) | |
| *A61K 9/08* | (2006.01) | |
| *A61K 47/54* | (2017.01) | |
| *A61K 47/18* | (2017.01) | |
| *A61K 47/26* | (2006.01) | |
| *A61K 47/44* | (2017.01) | |

(52) U.S. Cl.
CPC ........ *A61K 31/7068* (2013.01); *A61K 9/0019* (2013.01); *A61K 9/08* (2013.01); *A61K 47/16* (2013.01); *A61K 47/18* (2013.01); *A61K 47/20* (2013.01); *A61K 47/22* (2013.01); *A61K 47/26* (2013.01); *A61K 47/44* (2013.01); *A61K 47/548* (2017.08)

(58) Field of Classification Search
None
See application file for complete search history.

(56) References Cited

U.S. PATENT DOCUMENTS

| | | | |
|---|---|---|---|
| 7,951,787 B2 | 5/2011 | McGuigan | |
| 9,834,577 B2 | 12/2017 | Dammalapati et al. | |
| 10,117,888 B2 * | 11/2018 | Griffith | .................. A61K 47/18 |
| 10,786,523 B2 * | 9/2020 | Griffith | .................. A61P 35/00 |
| 11,040,051 B2 * | 6/2021 | Griffith | .................. A61K 47/20 |
| 2003/0109697 A1 | 6/2003 | Shepard et al. | |
| 2017/0107246 A1 | 4/2017 | Griffith et al. | |
| 2017/0226147 A1 | 8/2017 | Griffith | |
| 2018/0271889 A1 | 9/2018 | Griffith | |
| 2018/0273575 A1 | 9/2018 | McGuigan et al. | |
| 2018/0289733 A1 | 10/2018 | Griffith et al. | |
| 2018/0362571 A1 | 12/2018 | Kotala et al. | |
| 2018/0369266 A1 | 12/2018 | Kennovin et al. | |
| 2020/0397810 A1 | 12/2020 | Griffith et al. | |

FOREIGN PATENT DOCUMENTS

| | | |
|---|---|---|
| CN | 102740833 A | 10/2012 |
| JP | 2008528611 A | 7/2008 |
| JP | 2009528276 A | 8/2009 |
| WO | WO 99/37753 A1 | 7/1999 |
| WO | WO 2001/007454 A1 | 2/2001 |
| WO | WO 2005/012327 A2 | 2/2005 |
| WO | WO 2006/081363 A2 | 8/2006 |
| WO | WO 2007/092620 A2 | 8/2007 |
| WO | WO 2008/087488 A2 | 7/2008 |
| WO | WO 2011/062503 A1 | 5/2011 |
| WO | WO 2013/107515 A1 | 7/2013 |
| WO | WO 2014/076490 A1 | 5/2014 |
| WO | WO 2015/081133 A2 | 6/2015 |
| WO | WO 2015/198058 A1 | 12/2015 |
| WO | WO 2015/198059 A1 | 12/2015 |

(Continued)

OTHER PUBLICATIONS

Bilir, A., et al.; "Acetaminophen and DMSO modulate growth of gemcitabine cytotoxicity in FM3A Breast Cancer Cells in vitro," Neoplasma vol. 51, No. 6, p. 460-464 (2004).
Harris et al., "Synthesis and antiviral evaluation of phosphoramidate derivatives of (E)-5-(2-bromovinyl)-2'-deoxyuridine," Antiviral Chemistry & Chemotherapy, 12:293-300 (2002).
International Search Report and Written Opinion for International Application No. PCT/GB2015/051858 dated Aug. 13, 2015.
Lackey et al., "Enzyme-catalyzed therapeutic agent (ECTA) design: activation of the antitumor ECTA compound NB1011 by thymidylate synthase," Biochemical Pharmacology 61 :179-189 (2001).

(Continued)

*Primary Examiner* — Traviss C McIntosh, III

(74) *Attorney, Agent, or Firm* — Knowles Intellectual Property Strategies, LLC

(57) ABSTRACT

This invention relates to pharmaceutical formulations of gemcitabine-[phenyl-benzoxy-L-alaninyl)]-phosphate, a monophosphate derivative of the well-known oncology drug gemcitabine. In particular, the invention relates to formulations which comprise a polar aprotic solvent, preferably dimethyl acetamide (DMA). Formulations comprising these solvent provide therapeutically effective treatments of gemcitabine-[phenyl-benzoxy-L-alaninyl)]-phosphate. The invention also relates to methods of using said formulations and kits comprising said formulations.

11 Claims, No Drawings

(56) References Cited

FOREIGN PATENT DOCUMENTS

| WO | WO 2016/012781 A1 | 1/2016 |
|---|---|---|
| WO | WO 2016/055769 A1 | 4/2016 |
| WO | WO 2016/181093 A1 | 11/2016 |
| WO | WO 2017/060661 A1 | 4/2017 |
| WO | WO 2017/098252 A1 | 6/2017 |
| WO | WO 2017/109444 A1 | 6/2017 |
| WO | WO 2017/109485 A1 | 6/2017 |
| WO | WO 2017/109486 A1 | 6/2017 |
| WO | WO 2017/109491 A1 | 6/2017 |
| WO | WO 2018/229495 A1 | 12/2018 |

OTHER PUBLICATIONS

McGuigan et al., "Synthesis and evaluation of some masked phosphate esters of the anti-herpesvirus drug 882C (netivudine) as potential antiviral agents," Antiviral Chemistry & Chemotherapy 9:233-243 (1998).

Mcintee et al., "Amino Acid Phosphoramidate Nucleosides: Potential ADEPT/GDEPT Substrates," Bioorganic & Medicinal Chemistry Letters, 11:2803-2805 (2001).

Moysan et al., "An innovative hydrogel of gemcitabine-loaded lipid nanocapsules: when the drug is a key player of the nanomedicine structure," Soft Matter, 1 O: 1767-1777 (2014).

Siddiqui et al., "Design and Synthesis of Lipophilic Phosphoramidate d4T-MP Prodrugs Expressing High Potency Against HIV in Cell Culture: Structural Determinants for in Vitro Activity and QSAR," Journal of Medicinal Chemistry, 42(20): 4122-4128 (1999).

Slusarczyk, M. et al., "Application of ProTide Technology to Gemcitabine: A Successful Approach to Overcome the Key Cancer Resistance Mechanisms Leads to a New Agent (NUC-1031) in Clinical Development," J Med Chem, 57(4): 1531-1542 (2014).

United Kingdom Search Report for United Kingdom Application No. GB 1417646.5, dated May 29, 2015.

U.S. Pat. No. 9,834,577, B2, U.S. Appl. No. 15/753,237, Dammalapati, Dec. 5, 2017.

U.S. Pat. No. 10,005,810, B2, U.S. Appl. No. 16/065,369, Griffith, Jul. 5, 2022.

U.S. Pat. No. 10,117,888, B2, U.S. Appl. No. 16/060,681, Griffith et al., Nov. 6, 2018.

U.S. Pat. No. 10,660,912, B2, U.S. Appl. No. 15/411,409, Griffith, May 26, 2020.

U.S. Pat. No. 10,662,213, B2, U.S. Appl. No. 15/994,378, Griffith et al., May 26, 2020.

U.S. Pat. No. 10,669,300, B2, U.S. Appl. No. 15/514,673, Griffith, Jun. 2, 2020.

U.S. Pat. No. 10,774,104, B2, U.S. Appl. No. 15/308,475, Kotala et al., Sep. 15, 2020.

U.S. Pat. No. 10,786,523, B2, U.S. Appl. No. 16/142,948, Griffith et al., Sep. 29, 2020.

U.S. Pat. No. 11,040,051, B2, U.S. Appl. No. 17/010,338, Griffith et al., Jun. 22, 2021.

U.S. Pat. No. 11,040,997, B2, U.S. Appl. No. 15/308,491, McGuigan et al., Jun. 22, 2021.

U.S. Pat. No. 11,377,467, B2, U.S. Appl. No. 14/442,987, Griffith, Jul. 5, 2022.

2019/0022117, A1, U.S. Appl. No. 16/065,498, Griffith, Jan. 24, 2019.

2019/0381084, A1, U.S. Appl. No. 16/065,476, Griffith, Dec. 19, 2019.

2020/0197430, A1, U.S. Appl. No. 16/642,832, Griffith, Jun. 25, 2020.

2020/0262861, A1, U.S. Appl. No. 16/865,527, Griffith, Aug. 20, 2020.

2020/0268783, A1, U.S. Appl. No. 16/871,140, Griffith, Aug. 27, 2020.

2021/0009625, A1, U.S. Appl. No. 16/991,765, Kotala et al., Jan. 14, 2021.

2021/0100825, A1, U.S. Appl. No. 17/028,314, Griffith et al., Apr. 8, 2021.

2022/0031727, A1, U.S. Appl. No. 17/324,835, Griffith et al., Feb. 3, 2022.

2022/0033433, A1, U.S. Appl. No. 17/323,367, McGuigan et al., Feb. 3, 2022.

U.S. Appl. No. 17/532,914, Griffith et al., filed Nov. 22, 2021.

U.S. Appl. No. 17/845,878, Griffith et al., filed Jun. 21, 2022.

U.S. Appl. No. 17/883,472, Griffith et al., filed Aug. 8, 2022.

* cited by examiner

FORMULATION COMPRISING A GEMCITABINE-PRODRUG

RELATED APPLICATIONS

This application is a continuation of U.S. patent application Ser. No. 17/010,338, filed Sep. 2, 2020; which is a continuation of U.S. patent application Ser. No. 16/142,948, filed Sep. 26, 2018, now U.S. Pat. No. 10,786,523; which is a continuation of U.S. patent application Ser. No. 15/308,475, filed Nov. 2, 2016, now U.S. Pat. No. 10,117,888; which is a § 371 national stage application based on Patent Cooperation Treaty Application serial number PCT/GB2015/051858, filed Jun. 25, 2015; which claims the benefit of priority to GB 1411253.6, filed Jun. 25, 2014; IN 2050/MUM/2014, filed Jun. 25, 2014; and GB 1417646.5, filed Oct. 6, 2014.

This invention relates to pharmaceutical formulations of gemcitabine-[phenyl-benzoxy-L-alaninyl)]-phosphate (chemical name: 2'-Deoxy-2',2'-difluoro-D-cytidine-5'-O-[phenyl (benzoxy-L-alaninyl)]phosphate), a monophosphate derivative of the well-known oncology drug gemcitabine. In particular, the invention relates to formulations which comprise a polar aprotic solvent, preferably dimethyl acetamide (DMA). Formulations comprising these solvents provide therapeutically effective treatments of gemcitabine-[phenyl-benzoxy-L-alaninyl)]-phosphate. The formulations of the invention may be diluted to the required concentration shortly before administration.

BACKGROUND

Gemcitabine (1; marketed as Gemzar®) is an effective nucleoside analogue that is currently approved to treat breast, non-small cell lung, ovarian and pancreatic cancers and widely used to treat a variety of other cancers including bladder, biliary, colorectal and lymphoma.

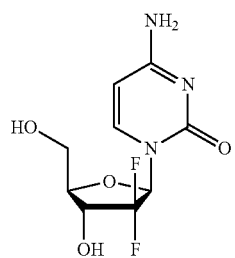

Gemcitabine's clinical utility is limited by a number of inherent and acquired resistance mechanisms. At the cellular level resistance is dependent on three parameters: (i) the down-regulation of deoxycytidine kinase, necessary for the activation into the phosphorylated moiety; (ii) the reduced expression of nucleoside transporters, in particular, hENT1 required for uptake by cancer cells; and (iii) the up-regulation of catalytic enzymes especially cytidine deaminase that degrades gemcitabine.

WO2005/012327 describes a series of phosphate derivatives of gemcitabine and related nucleoside drug molecules. Among them gemcitabine-[phenyl-benzoxy-L-alaninyl)]-phosphate (NUC-1031; 2) is identified as a particularly effective compound. These compounds appear to avoid many of the inherent and acquired resistance mechanisms which limit the utility of gemcitabine ('*Application of Pro Tide Technology to Gemcitabine: A Successful Approach to Overcome the Key Cancer Resistance Mechanisms Leads to a New Agent (NUC-1031) in Clinical Development*'; Slusarczyk et all; *J. Med. Chem.*; 2014, 57, 1531-1542).

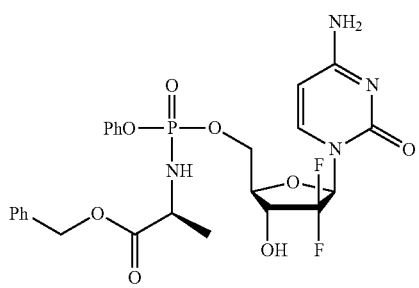

Unfortunately, NUC-1031 is extremely lipophillic and thus poorly water soluble (by calculation: <0.1 mg/mL), and the ionisable moieties, pyrimidine nitrogen and phenolic hydroxyl, have calculated pKa values which lie out-side the pH range suitable for parenteral administration. It is essentially insoluble in water, regardless of salt content or pH, and this has serious implications for the development of clinically acceptable methods for delivering the compound at sufficiently high dosages for effective treatment. Sometimes, the delivery of drug molecules as lipophillic as NUC-1031 can be achieved but only with an unacceptable level of pain to the patient.

NUC-1031 exists as a mixture of two diastereoisomers, epimeric at the phosphate centre:

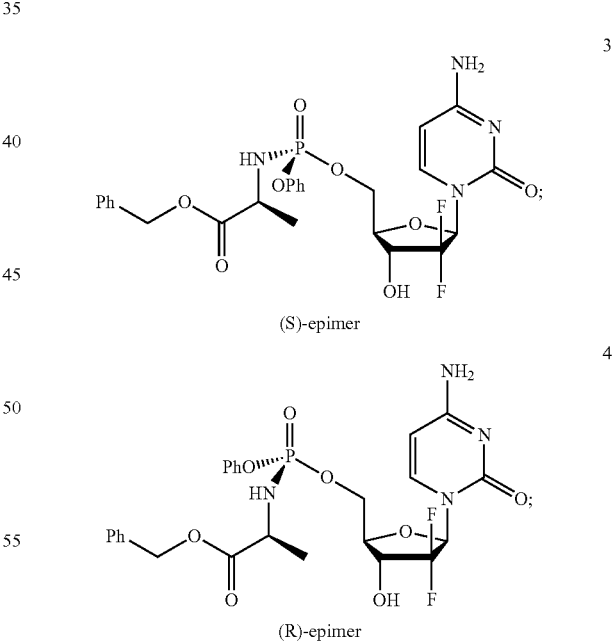

It is an aim of certain embodiments of this invention to provide a pharmaceutical formulation of gemcitabine-[phenyl-benzoxy-L-alaninyl)]-phosphate which delivers an effective dose.

It is an aim of certain embodiments of this invention to provide a stable pharmaceutical formulation of gemcitabine-[phenyl-benzoxy-L-alaninyl)]-phosphate. For intravenous administration, suitable infusion formulations typically should be stable for greater than 30 minutes and up to 48 hours. Typically, for intravenous administration the formulation should be stable both to precipitation of gemcitabine-[phenyl-benzoxy-L-alaninyl)]-phosphate and to degradation of gemcitabine-[phenyl-benzoxy-L-alaninyl)]-phosphate.

It is an aim of certain embodiments of this invention to provide a pharmaceutical formulation of gemcitabine-[phenyl-benzoxy-L-alaninyl)]-phosphate which delivers an effective dose intravenously.

It is an aim of certain embodiments of this invention to provide a parenteral formulation of gemcitabine-[phenyl-benzoxy-L-alaninyl)]-phosphate which can be administered in either a peripheral vein or via a central line. Thus, it is an aim of certain embodiments of this invention to provide a formulation which has an osmolarity which is acceptable for administration via a peripheral vein.

Certain embodiments of this invention satisfy some or all of the above aims.

BRIEF SUMMARY OF THE DISCLOSURE

In accordance with a first aspect of the present invention there is provided a pharmaceutical formulation comprising:
  gemcitabine-[phenyl-benzoxy-L-alaninyl)]-phosphate;
  a polar aprotic solvent; and
  optionally one or more pharmaceutically acceptable excipients.

The polar aprotic solvent may be selected from dimethylacetamide (DMA) dimethylsulfoxide (DMSO) and N-methypyrrolidone (NMP). Preferably, the polar aprotic solvent is DMA. DMA offers the best solubility profile of those tested.

The polar aprotic solvent (e.g. DMA, DMSO or NMP) may be pharmaceutical grade. The polar aprotic solvent (e.g. DMA) may be the administration vehicle or it may be that the formulation is diluted before use with an administration vehicle which provides desirable characteristics. Thus, the formulation may be ready for infusion and have the polar aprotic solvent (e.g. DMA) as a major component; or it may be a formulation which has the polar aprotic solvent (e.g. DMA) as a major component and is intended to be diluted before administration to generate a formulation which is ready for infusion and has the polar aprotic solvent (e.g. DMA) only as a minor component; or it may be a formulation which is ready for infusion, has the polar aprotic solvent (e.g. DMA) only as a minor component and results from the dilution of a formulation in which polar aprotic solvent (e.g. DMA) is a major component. Thus, the polar aprotic solvent (e.g. DMA) may represent from 0.1% v/v to 100% v/v of the formulation.

Very few pharmaceutically acceptable solvents dissolve sufficient quantities of gemcitabine-[phenyl-benzoxy-L-alaninyl)]-phosphate to deliver a therapeutically effective dose intravenously. Of those that do, many are not stable, i.e. the gemcitabine-[phenyl-benzoxy-L-alaninyl)]-phosphate will tend to precipitate out of solution. The inventors have surprisingly found that solvents which do generate a stable solution are generally polar aprotic solvents, for example DMA, DMSO and NMP. Of those solvents that have been found to be capable of dissolving gemcitabine-[phenyl-benzoxy-L-alaninyl)]-phosphate, the inventors have found that certain polar aprotic solvents, and in particular DMA, are particularly able to hold it in solution at a concentration necessary to deliver the required dose when that solution is diluted with an aqueous vehicle. Thus, the use of polar aprotic solvents, and in particular DMA, provides a twofold advantage over other formulation solvents which, surprisingly, makes it an excellent medium for delivering gemcitabine-[phenyl-benzoxy-L-alaninyl)]-phosphate to patients in a practical and therapeutically effective manner.

The gemcitabine-[phenyl-benzoxy-L-alaninyl)]-phosphate may be present as a mixture of phosphate diastereoisomers or it may be present as the (S)-epimer or as the (R)-epimer in substantially diastereomerically pure form. 'Substantially diastereomerically pure' is defined for the purposes of this invention as a diastereomeric purity of greater than about 90%. If present as a substantially diastereoisomerically pure form, the gemcitabine-[phenyl-benzoxy-L-alaninyl)]-phosphate may have a diastereoisomeric purity of greater than 95%, 98%, 99%, or even 99.5%.

The gemcitabine-[phenyl-benzoxy-L-alaninyl)]-phosphate may be present as a mixture of phosphate diastereoisomers. Administering NUC-1031 as a mixture of diastereoisomers thus offers a practical and economic method of delivering an effective treatment. Non clinical evidence suggests that there is no difference in biological effectiveness between the two isomers.

Alternatively, the gemcitabine-[phenyl-benzoxy-L-alaninyl)]-phosphate 2 may be present as the (S)-epimer 3 in substantially diastereomerically pure form. The (S)-epimer shows a surprising and remarkable increase in solubility relative to the (R)-epimer which allows more convenient formulation, increases the stability of the formulation and reduces the risk of precipitation in the giving sets or central line. It may also allow the drug to be delivered in such a way as to reduce patient discomfort when administered via a peripheral vein in a diluted formulation.

The formulation of the invention may be for dilution by a predetermined amount shortly before administration, i.e. up to 48 hours (e.g. up to 24, 12 or 2 hours) before administration.

The formulation may also comprise one or more pharmaceutically acceptable solubilizers, e.g. a pharmaceutically acceptable non-ionic solubilizers. Solubilizers may also be called surfactants. Illustrative solubilizers include polyethoxylated fatty acids and fatty acid esters and mixtures thereof. Suitable solubilizers include polyethoxylated castor oil (e.g. that sold under the trade name Kolliphor® ELP); or polyethoxylated stearic acid (e.g. that sold under the trade names Solutol® or Kolliphor® HS15); or polyethoxylated (e.g. polyoxyethylene (20)) sorbitan monooleate, (e.g. that sold under the trade name Tween® 80).

In certain preferred embodiments, the formulation comprises more than one pharmaceutically acceptable solubilizer.

The formulation may also comprise an aqueous vehicle. The formulation of the invention may be ready to administer, in which case it will typically comprise an aqueous vehicle.

The formulation may be for parenteral, e.g. for intravenous, subcutaneous or intramuscular administration. Preferably, the formulation is for intravenous administration. The administration may be through a central vein or it may be through a peripheral vein.

The total dose of gemcitabine-[phenyl-benzoxy-L-alaninyl)]-phosphate in a formulation suitable for administration will typically be from 250 mg to 3 g, e.g. from 1 g to 2 g, e.g. about 1.5 g.

It may be that the polar aprotic solvent (e.g. DMA) represents 30% or more by volume of the formulation. Thus, it may be that the polar aprotic solvent (e.g. DMA) represents 50% or more, e.g. 60% or more by volume of the formulation. The polar aprotic solvent (e.g. DMA) may represent 95% or less by volume of the formulation, e.g.

90% or less. The formulation may also comprise an aqueous vehicle (e.g. saline). The aqueous vehicle may be present in 50% or less by volume of the formulation, e.g. 30% or less by volume of the formulation. Typically the aqueous vehicle (e.g. saline) will represent 5% or more, e.g. 10% or more, by volume of the formulation.

It may be that the concentration of the gemcitabine-[phenyl-benzoxy-L-alaninyl)]-phosphate in the formulation solvent(s) is 500 mg or less per mL. It may be that the concentration 100 mg or more per mL. Preferably, the concentration is from 200 mg to 300 mg, e.g. from 225 mg to 275 mg, e.g. about 250 mg, per mL.

Certain preferred formulations comprise:
from 30% to 95% by volume DMA;
from 5% to 50% by volume aqueous vehicle; and
from 100 mg to 400 mg (e.g. from 100 mg to 300 mg) per mL gemcitabine-[phenyl-benzoxy-L-alaninyl)]-phosphate.

More preferred formulations comprise:
from 70% to 90% by volume DMA;
from 10% to 30% by volume aqueous vehicle (e.g. saline); and
from 200 mg to 300 mg per mL gemcitabine-[phenyl-benzoxy-L-alaninyl)]-phosphate.

The formulations described in the previous four paragraphs, in which the polar aprotic solvent (e.g. DMA) is present as a major component, may, for example, be used for administering gemcitabine-[phenyl-benzoxy-L-alaninyl)]-phosphate in the form of a mixture of phosphate diastereoisomers. They can also be used to administer gemcitabine-[phenyl-benzoxy-L-alaninyl)]-phosphate in the form of the (S)-phosphate epimer in substantially diastereomerically pure form. The formulations described in these paragraphs can be used by administering (e.g. by infusion or injection) the formulation without it being diluted prior to administration. They may be administered through a central vein.

Alternatively, these formulations may be diluted to form a formulation suitable for administration through a peripheral vein.

It may be that the polar aprotic solvent (e.g. DMA) represents 10% or more, e.g. 20% or more by volume of the formulation. Thus, it may be that the polar aprotic solvent (e.g. DMA) represents 80% or less, e.g. 60% or less by volume of the formulation. The polar aprotic solvent (e.g. DMA) may represent 40% or less by volume of the formulation. The formulation may also comprise one or more solubilizers (e.g. one or more polyethoxylated fatty acids). The one or more solubilizers may represent 90% or less by volume of the formulation, e.g. 80% or less by volume of the formulation. Typically the one or more solubilizers will represent 30% or more, e.g. 50% or more or 60% or more, by volume of the formulation. One preferred formulation comprises the drug as a solution in a 30%:70% DMA:solubilizer mixture.

It may be that the concentration of the gemcitabine-[phenyl-benzoxy-L-alaninyl)]-phosphate in the formulation solvent(s) is 200 mg or less per mL, e.g. 150 mg or less or 120 mg or less. It may be that the concentration is 40 mg or more per mL, e.g. 60 mg or more. Preferably, the concentration is from 70 mg to 110 mg, e.g. about 75 mg or about 100 mg, per mL.

Certain preferred formulations comprise:
from 20% to 80% by volume DMA;
from 30% to 80% by volume solubilizer or solubilizers; and
from 50 mg to 150 mg per mL gemcitabine-[phenyl-benzoxy-L-alaninyl)]-phosphate. The formulation may also comprise an aqueous vehicle, e.g. in an amount from 1% to 15% by volume.

Certain particularly preferred formulations comprise:
from 20% to 80% by volume DMA;
from 20% to 60% by volume a first solubilizer;
from 5% to 40% by volume a second solubilizer;
from 2% to 12% an aqueous vehicle; and
from 50 mg to 150 mg per mL gemcitabine-[phenyl-benzoxy-L-alaninyl)]-phosphate. The first solubilizer may be a polyethoxylated castor oil (e.g. that sold under the trade name Kolliphor® ELP). The second solubilizer may be a polyethoxylated sorbitan monooleate (e.g. that sold under the trade name Tween® 80). The formulation may also comprise an aqueous vehicle, e.g. in an amount from 3% to 15% by volume.

The formulation may comprise:
from 50% to 60% by volume DMA;
from 20% to 30% by volume the first solubilizer;
from 8% to 15% by volume the second solubilizer;
from 4% to 10% an aqueous vehicle; and
from 75 mg to 125 mg per mL gemcitabine-[phenyl-benzoxy-L-alaninyl)]-phosphate.

The formulations described in the previous five paragraphs, in which the polar aprotic solvent (e.g. DMA) is present as a major component, can be used, for example, for administering gemcitabine-[phenyl-benzoxy-L-alaninyl)]-phosphate in the form of the (S)-phosphate epimer in substantially diastereomerically pure form. They can also be used for administering a mixture of R and S epimers or the R epimer. The formulations described in these paragraphs are typically diluted with an aqueous vehicle prior to administration. Once diluted, they may be administered through a peripheral vein.

These formulations may be formed by diluting a formulation that does not contain any solubilizers. Gemcitabine-[phenyl-benzoxy-L-alaninyl)]-phosphate can degrade in the presence of certain solubilizers.

It may be that the polar aprotic solvent (e.g. DMA) represents 0.1% or more, e.g. 0.5% or more or 1% or more by volume of the formulation. Thus, it may be that DMA represents 10% or less, e.g. 5% or less or 3% or less by volume of the formulation. The polar aprotic solvent (e.g. DMA) may represent 8% or less or 2% or less by volume of the formulation. The formulation may also comprise an aqueous vehicle (e.g. WFI). The aqueous vehicle may be present in 99.5% or less by volume of the formulation, e.g. 99% or 98% or less by volume of the formulation. Typically the aqueous vehicle will represent 85% or more, e.g. 90% or more or 95% or more, by volume of the formulation. The formulation may also comprise one or more solubilizers (e.g. one or more polyethoxylated fatty acids). The one or more solubilizers may represent in 10% or less by volume of the formulation, e.g. 7.5% or less or 5% or less or 3% or less by volume of the formulation. Typically the one or more solubilizers will represent 0.1% or more, e.g. 0.5% or more or 1% or more or 2% or more, by volume of the formulation.

It may be that the concentration of the gemcitabine-[phenyl-benzoxy-L-alaninyl)]-phosphate in the formulation solvent(s) is 12.0 mg or less per mL or 10.0 mg or less per mL, e.g. 7.0 mg or less or 4.5 mg or less per mL. It may be that the concentration is 1.0 mg or more per mL, e.g. 2.0 mg or more. Preferably, the concentration is from 2.5 mg to 11 mg per mL, e.g. from 3 mg to 7 mg per mL, e.g. about 4.5 mg per mL.

Certain preferred formulations comprise:
from 0.1% to 15% (e.g. 0.5 to 5%) by volume DMA;
from 0.1% to 15% (e.g. 0.1% to 7.5%) by volume solubilizer or solubilizers;
from 85% to 99% by volume aqueous vehicle; and
from 2.0 mg to 12.0 mg (e.g. from 2.0 mg to 10.0 mg) per mL gemcitabine-[phenyl-benzoxy-L-alaninyl)]-phosphate.

Certain particularly preferred formulations comprise:
from 0.5% to 10% by volume DMA;
from 0.2% to 4% by volume a first solubilizer;
from 0.1% to 2% by volume a second solubilizer;
from 85% to 99% by volume aqueous vehicle; and
from 2.0 mg to 12.0 mg (e.g. from 2.0 mg to 10.0 mg) per mL gemcitabine-[phenyl-benzoxy-L-alaninyl)]-phosphate. The first solubilizer may be a polyethoxylated castor oil (e.g. that sold under the trade name Kolliphor® ELP). The second solubilizer may be a polyethoxylated sorbitan monooleate (e.g. that sold under the trade name Tween® 80).

The formulation may comprise:
from 0.5% to 6% by volume DMA;
from 0.5% to 6% by volume a first solubilizer;
from 0.2% to 4% by volume a second solubilizer;
from 85% to 99% by volume aqueous vehicle; and
from 2.0 mg to 12.0 mg (e.g. from 2.0 mg to 10.0 mg) per mL gemcitabine-[phenyl-benzoxy-L-alaninyl)]-phosphate.

The formulations described in the previous four paragraphs, in which the polar aprotic solvent (e.g. DMA) is present as a minor component, can be used, for example, for administering gemcitabine-[phenyl-benzoxy-L-alaninyl)]-phosphate in the form of the (S)-phosphate epimer in substantially diastereomerically pure form. They can also be used for administering a mixture of R and S epimers or the R epimer. The formulations described in these paragraphs will typically have been prepared by diluting a concentrated polar aprotic solvent (e.g. DMA) formulation or concentrated polar aprotic solvent (e.g. DMA) and solubilizer formulation with the aqueous vehicle up to 48 hours prior to administration. The resulting formulations may be administered through a peripheral vein.

While the formulations of the invention are preferably for parenteral administration, certain embodiments of the invention may also be administered orally.

In a second aspect of the invention is provided a pharmaceutical formulation comprising:
gemcitabine-[phenyl-benzoxy-L-alaninyl)]-phosphate;
a polar aprotic solvent (e.g. DMA); and
optionally one or more pharmaceutically acceptable excipients;
wherein the formulation is for medical use.

In a third aspect of the invention is provided a pharmaceutical formulation comprising:
gemcitabine-[phenyl-benzoxy-L-alaninyl)]-phosphate;
a polar aprotic solvent (e.g. DMA); and
optionally one or more pharmaceutically acceptable excipients;
wherein the formulation is for use in treating cancer.

In a fourth aspect of the invention is provided a method of treating cancer, the method comprising administering to a subject in need thereof a pharmaceutical formulation comprising:
gemcitabine-[phenyl-benzoxy-L-alaninyl)]-phosphate;
a polar aprotic solvent (e.g. DMA); and
optionally one or more pharmaceutically acceptable excipients.

The method may comprise the steps of;
diluting a solution comprising gemcitabine-[phenyl-benzoxy-L-alaninyl)]-phosphate, a polar aprotic solvent (e.g. DMA) and optionally one or more pharmaceutically acceptable excipients with an aqueous vehicle to provide a formulation for infusion or injection; and
administering the formulation for infusion or injection to the subject by infusion or injection.

The method may comprise the steps of;
diluting a first solution comprising gemcitabine-[phenyl-benzoxy-L-alaninyl)]-phosphate and a polar aprotic solvent (e.g. DMA) and optionally an aqueous vehicle with a second solution comprising a polar aprotic solvent (e.g. DMA) and one or more solubilizers to form a third solution;
diluting the third solution with an aqueous vehicle to provide a formulation for infusion or injection; and
administering the formulation for infusion or injection to the subject by infusion or injection.

The second formulation may comprise more than one solubilizer. Typically, the second formulation will not comprise an active.

The or each dilution may be by a predetermined amount.

The starting solution may be a formulation of the first aspect. Likewise, the formulation for infusion or injection may be a formulation of the first aspect. It may be that the administration step is carried out up to 48 hours (e.g. up to 12 or 2 hours) after the dilution step, e.g. the first or second dilution step.

The cancer may be a cancer selected from: pancreatic cancer, breast cancer, ovarian cancer, bladder cancer, colorectal cancer, lung cancer, bladder cancer, prostate cancer, cholangiocarcinoma, renal cancer, cervical cancer, thymic cancer, a cancer of an unknown primary origin, lymphoma or leukaemia.

The method may comprise:
a flushing a central line intravenous administration device with a first portion of a first formulation, the first formulation comprising:
from 30% to 95% by volume DMA;
from 5% to 50% by volume aqueous vehicle; and
administering a second formulation to the patient via the administration device, the second formulation comprising:
from 30% to 95% by volume DMA;
from 5% to 50% by volume aqueous vehicle; and
from 100 mg to 400 mg (e.g. from 100 mg to 300 mg) per mL gemcitabine-[phenyl-benzoxy-L-alaninyl)]-phosphate; and
optionally flushing the administration device with a second portion of the first formulation. Typically, the first formulation will not comprise an active. In a fifth aspect of the invention is provided a method of preparing a pharmaceutical formulation of gemcitabine-[phenyl-benzoxy-L-alaninyl)]-phosphate for infusion or injection, the method comprising:
diluting a solution comprising gemcitabine-[phenyl-benzoxy-L-alaninyl)]-phosphate, a polar aprotic solvent (e.g. DMA) and optionally one or more pharmaceutically acceptable excipients with an aqueous vehicle to provide the formulation for infusion or injection.

The dilution may be by a predetermined amount.

The starting solution may be a formulation of the first aspect. Likewise, the formulation for infusion or injection may be a formulation of the first aspect. It may be that the administration step is carried out up to 48 hours (e.g. up to 12 or 2 hours) after the dilution step.

The aqueous vehicle may be selected from saline (e.g. 0.9% saline or 0.45% saline), glucose solution and water for infusion (WFI). Preferably, the aqueous vehicle is WFI. The use of WFI provides a formulation which is substantially isotonic with blood.

The aqueous vehicle may comprise one or more pharmaceutically acceptable solubilizers (also known as a surfactants), e.g. a pharmaceutically acceptable non-ionic solubilizer. An exemplary solubilizer is polyoxyethylene (20) sorbitan monooleate (marketed as Tween® 80).

In a sixth aspect of the invention is provided a method of preparing a pharmaceutical formulation of gemcitabine-[phenyl-benzoxy-L-alaninyl)]-phosphate, the method comprising:
  dissolving gemcitabine-[phenyl-benzoxy-L-alaninyl)]-phosphate in a polar aprotic solvent (e.g. DMA) to form a solution;
  adding one or more further pharmaceutical excipients to the solution to form a pharmaceutical formulation of gemcitabine-[phenyl-benzoxy-L-alaninyl)]-phosphate.

The inventors have discovered that a more efficient process arises from predissolving the gemcitabine-[phenyl-benzoxy-L-alaninyl)]-phosphate in a polar aprotic solvent (e.g. DMA) and then adding the required excipients, e.g. solubilizers.

The one or more pharmaceutical excipients may include a solubilizer.

In a seventh aspect of the present invention is provided a pharmaceutical formulation comprising gemcitabine-[phenyl-benzoxy-L-alaninyl)]-(S)-phosphate, or a pharmaceutically acceptable salt or solvate thereof, and at least one pharmaceutically acceptable excipient. Preferably, the gemcitabine-[phenyl-benzoxy-L-alaninyl)]-(S)-phosphate is in substantially diastereoisomerically pure form.

The formulation may be for parenteral, e.g. for intravenous, subcutaneous or intramuscular administration. Preferably, the formulation is for intravenous administration.

The formulation may be an aqueous formulation which optionally also comprises a polar organic solvent. In the case of parenteral (e.g. intravenous) administration, the formulation preferably also comprises a polar organic solvent. The formulation may comprise DMSO or NMP.

The formulation may also comprise a cyclodextrin.

In a eighth aspect of the present invention is provided a pharmaceutical formulation comprising gemcitabine-[phenyl-benzoxy-L-alaninyl)]-(R)-phosphate, or a pharmaceutically acceptable salt or solvate thereof, and at least one pharmaceutically acceptable excipient. Preferably, the gemcitabine-[phenyl-benzoxy-L-alaninyl)]-(R)-phosphate is in substantially diastereoisomerically pure form.

In a ninth aspect of the invention is provided a kit, the kit comprising:
  a first formulation comprising:
    from 30% to 95% by volume DMA;
    from 5% to 50% by volume aqueous vehicle; and
  a second formulation comprising:
    from 30% to 95% by volume DMA;
    from 5% to 50% by volume aqueous vehicle; and
    from 100 mg to 400 mg (e.g. from 100 mg to 300 mg) per mL gemcitabine-[phenyl-benzoxy-L-alaninyl)]-phosphate.

The first formulation will typically not comprise an active. Thus, it will typically not comprise gemcitabine-[phenyl-benzoxy-L-alaninyl)]-phosphate. The first formulation may be provided in two separate vessels or in a single vessel.

The kit of the ninth aspect of the invention is useful for the intravenous administration of gemcitabine-[phenyl-benzoxy-L-alaninyl)]-phosphate via a central line. The central line is flushed with the first formulation prior to administration of the second formulation. This mitigates the risk of precipitation of gemcitabine-[phenyl-benzoxy-L-alaninyl)]-phosphate in or at the entrance to the intravenous administration apparatus, i.e. the central line, by avoiding the direct contact of the active formulation with aqueous media (e.g. a saline flushing solution). The central line may also be flushed with the first formulation after administration of the second formulation. This further prevents precipitation.

In a tenth aspect of the invention is provided a kit, the kit comprising:
  a first formulation comprising:
    from 30% to 95% by volume DMA;
    from 5% to 50% by volume aqueous vehicle; and
    from 100 mg to 400 mg (e.g. from 100 mg to 300 mg) per mL gemcitabine-[phenyl-benzoxy-L-alaninyl)]-phosphate; and
  a second formulation comprising:
    from 20% to 80% by volume DMA;
    from 20% to 60% by volume a first solubilizer;
    from 10% to 40% by volume a second solubilizer.

Typically the second formulation will not comprise any active. The kit is useful for the preparation of formulations suitable for peripheral administration. The first formulation is diluted with the second formulation up to 48 h, e.g. up to 24 h before administration to form a third formulation. The third formulation is further diluted with an aqueous vehicle before administration to the desired concentration to form the formulation which is used administered by infusion or injection to the patient. In order to achieve formulations for peripheral administration which are stable with respect to precipitation of gemcitabine-[phenyl-benzoxy-L-alaninyl)]-phosphate, it is typically desirable to include solubilizers. However, the gemcitabine-[phenyl-benzoxy-L-alaninyl)]-phosphate can be prone to degradation in the presence of such solubilizers. Thus, a two stage dilution method is, in certain embodiments of the invention, the preferable means by which formulations for peripheral administration are achieved.

DETAILED DESCRIPTION

Throughout this specification, the term S-epimer or S-diastereoisomer refers to gemcitabine-[phenyl-benzoxy-L-alaninyl)]-(S)-phosphate. Likewise, throughout this specification, the term R-epimer or R-diastereoisomer refers to gemcitabine-[phenyl-benzoxy-L-alaninyl)]-(R)-phosphate.

The term 'saline' is intended to refer to an aqueous solution of sodium chloride. Saline solutions of the present invention will typically be sterile and will typically be at a concentration suitable for use in parenteral administration. Suitable concentrations are up to 2 w/v % or up to 1 w/v %. To optimise osmolarity different concentrations of saline can be used in the formulations of the invention, e.g. 0.9% or 0.45%.

The formulations of the present invention can be used in the treatment of the human body. They may be used in the treatment of the animal body. In particular, the compounds of the present invention can be used to treat commercial animals such as livestock. Alternatively, the compounds of the present invention can be used to treat companion animals such as cats, dogs, etc.

The compounds in the formulations of the invention may be obtained, stored and/or administered in the form of a pharmaceutically acceptable salt. Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts. Hemisalts of acids and bases may also be formed, for example, hemisulfate, hemioxalate and hemicalcium salts. In certain embodiments, particularly those that apply to the s-epimer, the compound is in the form of a HCl salt or a hemioxalate salt. Preferably, the compound of the invention are not in the form of a salt, i.e. they are in the form of the free base/free acid.

For the above-mentioned formulations of the invention the dosage administered will, of course, vary with the compound employed, the precise mode of administration, the treatment desired and the disorder indicated. Dosage levels, dose frequency, and treatment durations of compounds of the invention are expected to differ depending on the formulation and clinical indication, age, and co-morbid medical conditions of the patient. The size of the dose for therapeutic purposes of compounds of the invention will naturally vary according to the nature and severity of the conditions, the age and sex of the animal or patient and the route of administration, according to well known principles of medicine.

A pharmaceutical formulation typically takes the form of a composition in which active compounds, or pharmaceutically acceptable salts thereof, are in association with a pharmaceutically acceptable adjuvant, diluent or carrier. One such pharmaceutically acceptable adjuvant, diluent or carrier in the formulations of the invention is the polar aprotic solvent. Conventional procedures for the selection and preparation of suitable pharmaceutical formulations are described in, for example, "Pharmaceuticals—The Science of Dosage Form Designs", M. E. Aulton, Churchill Livingstone, 1988.

The formulations may be suitable for topical application (e.g. to the skin or bladder), for oral administration or for parenteral (e.g. intravenous administration).

Any solvents used in pharmaceutical formulations of the invention should be pharmaceutical grade, by which it is meant that they have an impurity profile which renders them suitable for administration (e.g. intravenous administration) to humans.

For oral administration the formulations of the invention may comprise the active compound admixed with an adjuvant or a carrier, for example, lactose, saccharose, sorbitol, mannitol; a starch, for example, potato starch, corn starch or amylopectin; a cellulose derivative; a binder, for example, gelatine or polyvinylpyrrolidone; and/or a lubricant, for example, magnesium stearate, calcium stearate, polyethylene glycol, a wax, paraffin, and the like, and then compressed into tablets. If coated tablets are required, the cores, prepared as described above, may be coated with a concentrated sugar solution which may contain, for example, gum arabic, gelatine, talcum and titanium dioxide. Alternatively, the tablet may be coated with a suitable polymer dissolved in a readily volatile organic solvent.

For the preparation of soft gelatine capsules, the active compounds may be admixed with, for example, a vegetable oil or polyethylene glycol. Hard gelatine capsules may contain granules of the compound using either the above-mentioned excipients for tablets. Also liquid or semisolid formulations of the active compounds may be filled into hard gelatine capsules.

Liquid preparations for oral application may be in the form of syrups or suspensions, for example, solutions containing the compound of the invention, the balance being sugar and a mixture of ethanol, water, glycerol and propylene glycol. Optionally such liquid preparations may contain colouring agents, flavouring agents, sweetening agents (such as saccharine), preservative agents and/or carboxymethylcellulose as a thickening agent or other excipients known to those skilled in art.

Preferably, however the formulations of the invention are for parenteral (e.g. intravenous) administration or for dilution to form a formulation for parenteral (e.g. intravenous) administration. For parenteral (e.g. intravenous) administration the active compounds may be administered as a sterile aqueous or oily solution. Preferably, the active compounds are administered as a sterile aqueous solution.

The pharmaceutical composition of the invention will preferably comprise from 0.05 to 99% w (percent by weight) gemcitabine-[phenyl-benzoxy-L-alaninyl)]-phosphate, more preferably from 0.05 to 80% w gemcitabine-[phenyl-benzoxy-L-alaninyl)]-phosphate, still more preferably from 0.10 to 70% w gemcitabine-[phenyl-benzoxy-L-alaninyl)]-phosphate, and even more preferably from 0.10 to 50% w gemcitabine-[phenyl-benzoxy-L-alaninyl)]-phosphate, all percentages by weight being based on total composition.

Cyclodextrins have been shown to find wide application in drug delivery (Rasheed et al, *Sci. Pharm.*, 2008, 76, 567-598). Cyclodextrins are a family of cyclic oligosaccharides. They act as a 'molecular cage' which encapsulates drug molecules and alters properties of those drug molecules such as solubility. Cyclodextrins comprise ($\alpha$-1,4)-linked $\alpha$-D-glucopyranose units. Cyclodextrins may contains 6, 7 or 8 glucopyranose units (designated $\alpha$-, $\beta$- and $\gamma$-cyclodextrins respectively). Cyclodextrins used in pharmaceutical formulations are often $\beta$-cyclodextrins. The pendant hydroxyl groups can be alkylated with a $C_1$-$C_8$ substituted or unsubstituted alkyl group. Examples of cyclodextrins are $\alpha$-cyclodextrin, $\beta$-cyclodextrin, $\gamma$-cyclodextrin, 2-hydroxypropyl-$\beta$-cyclodextrin (HP-$\beta$-CD), sulfobutylether $\beta$-cyclodextrin sodium salt, partially methylated $\beta$-cyclodextrin. The formulations of the invention may also comprise at least one cyclodextrin.

The present invention also includes formulations of all pharmaceutically acceptable isotopically-labelled forms of compound wherein one or more atoms are replaced by atoms having the same atomic number, but an atomic mass or mass number different from the atomic mass or mass number of the predominant isotope usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds, for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Isotopically-labelled compounds can generally be prepared by conventional techniques known to those skilled in the art or by processes analogous to those described using an appropriate isotopically-labelled reagent in place of the non-labelled reagent previously employed.

The method of treatment or the formulation for use in the treatment of cancer, lymphoma or leukemia may involve, in addition to the formulations of the invention, conventional surgery or radiotherapy or chemotherapy. Such chemotherapy may include the administration of one or more other active agents.

Where a further active agent is administered as part of a method of treatment of the invention, such combination treatment may be achieved by way of the simultaneous, sequential or separate dosing of the individual components of the treatment. Such combination products employ the compounds of this invention within a therapeutically effective dosage range described hereinbefore and the one or more other pharmaceutically-active agent(s) within its approved dosage range.

Thus, the pharmaceutical formulations of the invention may comprise another active agent.

The one or more other active agents may be one or more of the following categories of anti-tumor agents:

(i) antiproliferative/antineoplastic drugs and combinations thereof, such as alkylating agents (for example cyclophosphamide, nitrogen mustard, bendamustin, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, pemetrexed, cytosine arabinoside, and hydroxyurea); antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); proteasome inhibitors, for example carfilzomib and bortezomib; interferon therapy; and topoisomerase inhibitors (for example epipodophyllotoxins like etoposide and teniposide, amsacrine, topotecan, mitoxantrone and camptothecin);

(ii) cytostatic agents such as antiestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents, for example dasatinib and bosutinib (SKI-606), and metalloproteinase inhibitors, inhibitors of urokinase plasminogen activator receptor function or antibodies to Heparanase;

(iv) inhibitors of growth factor function: for example such inhibitors include growth factor antibodies and growth factor receptor antibodies, for example the anti-erbB2 antibody trastuzumab [Herceptin™], the anti-EGFR antibody panitumumab, the anti-erbB1 antibody cetuximab, tyrosine kinase inhibitors, for example inhibitors of the epidermal growth factor family (for example EGFR family tyrosine kinase inhibitors such as gefitinib, erlotinib and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; modulators of protein regulators of cell apoptosis (for example Bcl-2 inhibitors); inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib, tipifarnib and lonafarnib), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor, kinase inhibitors; aurora kinase inhibitors and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™); thalidomide; lenalidomide; and for example, a VEGF receptor tyrosine kinase inhibitor such as vandetanib, vatalanib, sunitinib, axitinib and pazopanib;

(vi) gene therapy approaches, including for example approaches to replace aberrant genes such as aberrant p53 or aberrant BRCA1 or BRCA2;

(vii) immunotherapy approaches, including for example antibody therapy such as alemtuzumab, rituximab, ibritumomab tiuxetan (Zevalin®) and ofatumumab; interferons such as interferon α; interleukins such as IL-2 (aldesleukin); interleukin inhibitors for example IRAK4 inhibitors; cancer vaccines including prophylactic and treatment vaccines such as HPV vaccines, for example Gardasil, Cervarix, Oncophage and Sipuleucel-T (Provenge); and toll-like receptor modulators for example TLR-7 or TLR-9 agonists;

(viii) cytotoxic agents for example fludaribine (fludara), cladribine, pentostatin (Nipent™);

(ix) steroids such as corticosteroids, including glucocorticoids and mineralocorticoids, for example aclometasone, aclometasone dipropionate, aldosterone, amcinonide, beclomethasone, beclomethasone dipropionate, betamethasone, betamethasone dipropionate, betamethasone sodium phosphate, betamethasone valerate, budesonide, clobetasone, clobetasone butyrate, clobetasol propionate, coprednol, cortisone, cortisone acetate, cortivazol, deoxycortone, desonide, desoximetasone, dexamethasone, dexamethasone sodium phosphate, dexamethasone isonicotinate, difluorocortolone, fluclorolone, flumethasone, flunisolide, fluocinolone, fluocinolone acetonide, fluocinonide, fluocortin butyl, fluocortisone, fluocortolone, fluocortolone caproate, fluocortolone pivalate, fluorometholone, fluprednidene, fluprednidene acetate, flurandrenolone, fluticasone, fluticasone propionate, halcinonide, hydrocortisone, hydrocortisone acetate, hydrocortisone butyrate, hydrocortisone aceponate, hydrocortisone buteprate, hydrocortisone valerate, icomethasone, icomethasone enbutate, meprednisone, methylprednisolone, mometasone paramethasone, mometasone furoate monohydrate, prednicarbate, prednisolone, prednisone, tixocortol, tixocortol pivalate, triamcinolone, triamcinolone acetonide, triamcinolone alcohol and their respective pharmaceutically acceptable derivatives. A combination of steroids may be used, for example a combination of two or more steroids mentioned in this paragraph;

(x) targeted therapies, for example PI3Kd inhibitors, for example idelalisib and perifosine; or compounds that inhibit PD-1, PD-L1 and CAR T.

The one or more other active agents may also be antibiotic.

As an illustrative example, a diastereomeric mixture of gemcitabine-[phenyl-benzoxy-L-alaninyl)]-phosphate can be prepared according to the synthetic methods described in WO2005/012327 or those described in 'Application of Pro Tide Technology to Gemcitabine: A Successful Approach to Overcome th Key Cancer Resistance Mechanisms Leads to a New Agent (NUC-1031) in Clinical Development'; Slusarczyk et all; J. Med. Chem.; 2014, 57, 1531-1542.

The (R) and (S) isomers of gemcitabine-[phenyl-benzoxy-L-alaninyl)]-phosphate can be separated by HPLC under the following conditions:
Equipment: Agilent 1200™ series with DAD detector
Flow rate: 1.0 mL/min
Column: Chiralpak AD™; 250×4.6 mm ID (normal phase)
Temperature: ambient
Particle size: 20 μm
Feed: dissolved in MeOH; 10 g/L
Solvent: n-heptane/IPA 10 →50% IPA
The (S)-epimer eluted at 8.6 minutes and the (R)-epimer eluted at 10.3 minutes.

The individual isomers can be characterised using the following characterisation methods: Proton ($^1$H), carbon ($^{13}$C), phosphorus ($^{31}$P) and fluorine ($^{19}$F) NMR spectra were recorded on a Bruker Avance 500 spectrometer at 25° C. Spectra were auto-calibrated to the deuterated solvent peak and all $^{13}$C NMR and $^{31}$P NMR were proton-decoupled. The purity of final compounds was verified to be >95% by HPLC analysis using Varian Polaris C18-A (10 μM) as an analytic column with a gradient elution of H$_2$O/MeOH from 100/0 to 0/100 in 35 min. The HPLC analysis was conducted by Varian Prostar (LC Workstation-Varian prostar 335 LC detector).

2'-Deoxy-2',2'-difluoro-D-cytidine-5'-O-[phenyl (benzyloxy-L-alaninyl)]-(S)-phosphate 3

(ES+) m/z, found: (M+Na$^+$) 603.14. C$_{25}$H$_{27}$F$_2$N$_4$O$_8$NaP required: (M$^+$) 580.47.
$^{31}$P NMR (202 MHz, MeOD): δ$_P$ 3.66
$^1$H NMR (500 MHz, MeOD): δ$_H$ 7.58 (d, J=7.5 Hz, 1H, H-6), 7.38-7.32 (m, 7H, ArH), 7.26-7.20 (m, 3H, ArH), 6.24 (t, J=7.5 Hz, 1H, H-1'), 5.84 (d, J=7.5 Hz, 1H, H-5), 5.20 (AB system, J$_{AB}$=12.0 Hz, 2H, OCH$_2$Ph), 4.46-4.43 (m, 1H, H-5'), 4.36-4.31 (m, 1H, H-5'), 4.25-4.19 (m, 1H, H-3'), 4.07-4.00 (m, 2H, H-4', CHCH$_3$), 1.38 (d, J=7.2 Hz, 3H, CHCH$_3$).
$^{19}$F NMR (470 MHz, MeOD): δ$_F$ –118.0 (d, J=241 Hz, F), –120.24 (broad d, J=241 Hz, F).
$^{13}$C NMR (125 MHz, MeOD): δ$_C$ 174.61 (d, $^3$J$_{C—P}$=5.0 Hz, C=O, ester), 167.63 (C—NH$_2$), 157.74 (C=O base), 152.10 (d, $^2$J$_{C—P}$=7.0 Hz, C—Ar), 142.40 (CH-base), 137.22 (C—Ar), 130.90, 129.63, 129.39, 129.32, 126.32 (CH—Ar), 124.51 (d, $^1$J$_{C—F}$=257 Hz, CF$_2$), 121.47, 121.43 (CH—Ar), 96.67 (CH-base), 85.92 (broad signal, C-1'), 80.31 (C-4'), 71.27 (apparent t, $^2$J$_{C—F}$=23.7 Hz, C-3'), 68.03 (OCH$_2$Ph), 65.73 (d, $^2$J$_{C—P}$=5.30 Hz, C-5'), 51.66 (CHCH$_3$), 20.42 (d, $^3$J$_{C—P}$=6.25 Hz, CHCH$_3$).
Reverse HPLC, eluting with H$_2$O/MeOH from 100/0 to 0/100 in 35 min, showed one peak of diastereoisomer with t$_R$=22.53 min.

2'-deoxy-2',2'-difluoro-D-cytidine-5'-O-[phenyl(benzyloxy-L-alaninyl)]-(R)-phosphate 4

(ES+) m/z, found: (M+Na$^+$) 603.14. C$_{25}$H$_{27}$F$_2$N$_4$O$_8$NaP required: (M$^+$) 580.47.
$^{31}$P NMR (202 MHz, MeOD): δ$_P$ 3.83
$^1$H NMR (500 MHz, MeOD): δ$_H$ 7.56 (d, J=7.5 Hz, 1H, H-6), 7.38-7.31 (m, 7H, ArH), 7.23-7.19 (m, 3H, ArH), 6.26 (t, J=7.5 Hz, 1H, H-1'), 5.88 (d, J=7.5 Hz, 1H, H-5), 5.20 (s, 2H, OCH$_2$Ph), 4.49-4.46 (m, 1H, H-5'), 4.38-4.34 (m, 1H, H-5'), 4.23-4.17 (m, 1H, H-3'), 4.07-4.01 (m, 2H, H-4', CHCH$_3$), 1.38 (d, J=7.2 Hz, 3H, CHCH$_3$).
$^{19}$F NMR (470 MHz, MeOD): δ$_F$ –118.3 (d, J=241 Hz, F), –120.38 (broad d, J=241 Hz, F).
$^{13}$C NMR (125 MHz, MeOD): δ$_C$ 174.65 (d, $^3$J$_{C—P}$=5.0 Hz, C=O, ester), 167.65 (C—NH$_2$), 157.75 (C=O base), 152.10 (d, $^2$J$_{C—P}$=7.0 Hz, C—Ar), 142.28 (CH-base), 137.50 (C—Ar), 130.86, 129.63, 129.40, 129.32, 126.31 (CH—Ar), 124.50 (d, $^1$J$_{C—F}$=257 Hz, CF$_2$), 121.44, 121.40 (CH—Ar), 96.67 (CH-base), 85.90 (broad signal, C-1'), 80.27 (C-4'), 71.30 (apparent t, $^2$J$_{C—F}$=23.7 Hz, C-3'), 68.02 (OCH$_2$Ph), 65.50 (C-5'), 51.83 (CHCH$_3$), 20.22 (d, $^3$J$_{C—F}$=7.5 Hz, CHCH$_3$).
Reverse HPLC, eluting with H$_2$O/MeOH from 100/0 to 0/100 in 35 min, showed one peak of diastereoisomer with t$_R$=21.87 min Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The readers attention is directed to all papers and documents which are filed concurrently with or previous to this specification in connection with this application and which are open to public inspection with this specification, and the contents of all such papers and documents are incorporated herein by reference.

The following abbreviations are used in this specification:
API—active pharmaceutical ingredient, i.e. gemcitabine-[phenyl-benzoxy-L-alaninyl)]-phosphate

| | |
|---|---|
| DMA - dimethylacetamide | DMF - N,N-dimethylformamide |
| DMSO - dimethylsulfoxide | IPA - isopropyl alcohol |
| NMP - N-methylpyrroldinone | PEG - polyethylene glycol |

Example 1—Developing a First Generation Formulation

Gemcitabine-[phenyl-benzoxy-L-alaninyl)]-phosphate (NUC-1031; 2) was obtained as a mixture of phosphate diastereoisomers by the method described in WO2005/012327.

The experiments of Example 1 were all conducted using NUC-1031 as a mixture of phosphate diastereoisomers.

The solubility of NUC-1031 was determined in a range of pharmaceutically acceptable solvent systems. The protocol adopted was as follows:

A small volume, 1-2 mL, of each solvent system was prepared and a weight of the compound in question was added. The solutions were stirred for approximately 4 hours and then 0.45 μL membrane filtered. The concentration of the compound in question in the filtrate was then determined by HPLC assay.

Based on the gemcitabine dosage schedule used in the treatment of pancreatic cancer, the molecular weight adjusted dose of NUC-1031 would be about 3200 mg, given as an infusion once weekly. As an indication of the level of solubility required, taking a notional target of a 500 mL infusion volume, the required solubility of the NUC-1031 would be >6 mg/ml in the infusion fluid. However, this solubility level is just an indication and lower solubilities can still provide effective therapies.

TABLE 1 shows the solubility of gemcitabine-[phenyl-benzoxy-L-alaninyl)]-phosphate 2 in a range of solvents suitable for intravenous administration.

| Solvent | Appearance | Assay(mg/ml) |
|---|---|---|
| Ethanol | Solubilised quickly, after 30 minutes precipitated out to white paste | |
| Glycerol | API evident | |
| Propylene glycol | Precipitation evident after 30 minutes | 371 |
| PEG 400 | Precipitation evident after 120 minutes | 385 |
| NMP | Clear solution | >207 |
| DMSO | Clear solution | >217 |
| DMA | Clear solution | >656 |

DMSO, DMA and NMP, all of which are polar aprotic solvents, provided stable solutions.

After dilution 1:1 with water or saline NMP and DMA did not show any evidence of precipitation. Appendix 1 shows the solubility of NUC-1031 in a range of solvents on dilution. DMA provided sufficient solubility to administer the required dose

TABLE 2 shows the solubility of NUC-1031 in a range of solvents on dilution

| Solvent, quantity of NUC-1031 | Solvent: Saline (0.9%) | Appearance | NUC-1031 mg/mL HPLC assay filtrate | Recovery from theoretical | Evidence of further precipitation on storage of filtrate at RT >24 h |
|---|---|---|---|---|---|
| PEG 400, 91.2 mg/mL | 1:1 | Clear solution | n/a | n/a | Yes |
| PEG 400, 91.2 mg/mL | 1:2 | Precipitation evident | 16.2 | 53% | Yes |
| PEG 400, 91.2 mg/mL | 1:2* | Slightly turbid solution | 18.8 | 62% | Yes |
| PEG 400, 45.6 mg/mL | 1:1.5* | Clear solution | n/a | n/a | Yes |
| PEG 400, 45.6 mg/mL | 1:2* | Clear solution | n/a | n/a | Yes |
| PEG 400, 45.6 mg/mL | 1:2.5* | Precipitation, solution also precipitated after filtration | 10.5 | 80% | Yes |
| DMA 92.5 mg/mL | 1:1 glucose | Clear solution | 47.3 | 102% | No |
| DMA 92.5 mg/mL | 1:2 glucose | Slightly turbid solution | 29.7 | 96% | Yes |
| PEG 400 87.7 mg/mL | 1:1 glucose | Slightly turbid solution | 46.1 | 105% | Yes |
| PEG 400 87.7 mg/mL | 1:2 glucose | Turbid solution/ precipitation | 17.4 | 60% | No |
| NMP 115.0 mg/mL | 1:1 saline | Slightly turbid solution | 60.0 | 104% | No |
| NMP 115.0 mg/mL | 1:2 saline | Slightly turbid solution | 40.5 | 106% | Yes |
| NMP 115.0 mg/mL | 1:1 glucose | Slightly turbid solution | 58.5 | 102% | No |
| NMP 115.0 mg/mL | 1:2 glucose | Slightly turbid solution | 39.6 | 103% | Yes |
| DMA 91.6 mg/mL | 1:1 | Clear solution | 47.0 | 103% | |
| DMA 91.6 mg/mL | 1:2 | Slightly turbid solution | 30.2 | 99% | |
| DMA 91.6% mg/mL | 1:3 | Precipitation observed | 14.8 | 65% | |

TABLE 2-continued shows the solubility of NUC-1031 in a range of solvents on dilution

| Solvent, quantity of NUC-1031 | Solvent: Saline (0.9%) | Appearance | NUC-1031 mg/mL HPLC assay filtrate | Recovery from theoretical | Evidence of further precipitation on storage of filtrate at RT >24 h |
|---|---|---|---|---|---|
| DMA 91.6 mg/mL | 1:2* | Initially clear >30 min slight precipitation | 30.9 | 101% | |
| DMA 91.6 mg/mL | 1:3* | Precipitation evident | 15.2 | 66% | |
| DMA 73.3 mg/mL | 1:3* | Precipitation evident | 14.7 | 80% | |
| DMA 55.0 mg/mL | 1:3* | Slightly turbid solution | 13.9 | 101% | |
| DMA 45.8 mg/mL | 1:3* | Clear solution | 11.5 | 100% | |
| DMA 45.8 mg/mL | 1:3.5* | Clear solution | n/a | n/a | |
| DMA 45.8 mg/mL | 1:4* | Initially clear precipitates >30 min, stirring precipitate dissolves | 8.4 | 92% | |
| DMA 45.8 mg/mL | 1:4.5* | Slightly turbid solution | 7.2 | 87% | |

*0.9% saline containing 0.13% Tween 80

Effects of Dilution on DMA Solubility

Table 2 gives the effect of aqueous dilution on DMA solubility

TABLE 2

| Solution | Assay (mg/ml) | Precipitation > 24 hours |
|---|---|---|
| 100% DMA | 592 | No |
| 95:5 DMA:0.9% Saline | 518 | No |
| 90:10 DMA:0.9% Saline | 483 | No |
| 80:20 DMA:0.9% Saline | 386 | Yes |
| 70:30 DMA:0.9% Saline | 339 | Yes |
| 60:40 DMA:0.9% Saline | 293 | Yes |
| 50:50 DMA:0.9% Saline | 66 | Yes |

These DMA solutions were further evaluated for physical stability over a longer time and the results are given in Table 2a TABLE 2a

| Solution in 0.9% Saline | Assay (mg/ml) | Precipitation (2 weeks) |
|---|---|---|
| 80:20 DMA | 304 | Yes |
| 80:20 DMA | 272 | No |
| 80:20 DMA | 315 | Yes |
| 80:20 DMA | 270 | Yes |
| 85:15 DMA | 338 | No |

Following the experiments described above a formulation of 250 mg NUC-1031 in a 80:20 DMA:0.9% saline solution in a 5 ml vial was used in clinical testing. The formulation provided a successful treatment in the clinical study but needed to be administered by a central line because of pain on injection.

A formulation allowing administration by peripheral veins was then sought.

Example 2

The experiments of Examples 2 to 6 were all conducted using the (S)-epimer of NUC-1031.

Compounding

NUC-1031 was compounded into nine different formulations using DMA and a co-excipient as described in Table 3.

TABLE 3

NUC-1031 Formulations

| Formulation | NUC-1031 Weight | DMA Volume | Co-excipient | Co-excipient Volume |
|---|---|---|---|---|
| A | 1 g | 3 mL | Kolliphor ® EL | 7 mL |
| B | 1 g | 4 mL | Kolliphor ® EL | 6 mL |
| C | 1 g | 3 mL | Kolliphor ® ELP | 7 mL |
| D | 1 g | 4 mL | Kolliphor ® ELP | 6 mL |
| E | 1 g | 3 mL | Kolliphor ® HS15 | 7 mL |
| F | 1 g | 4 mL | Kolliphor ® HS15 | 6 mL |
| G | 1 g | 4 mL | PEG 400 | 6 mL |
| H | 1 g | 4 mL | PEG 300 | 6 mL |
| I | 1 g | 4 mL | Polyethylene Glycol | 6 mL |

The API was compounded using the following method:
1. The DMA was added to NUC-1031 in a glass scintillation vial. Instant dissolution of the API was observed.
2. The co-excipient was added second and briefly mixed (less than a minute) using a vortex mixer (Whirlmixer, Fisher brand).

It was found that this provided a more efficient method of compounding the API than dissolving NUC-1031 in a mixture of the DMA and the co-excipient. Dissolving the NUC-1031 in the mixture does still provide the compounded API but the process is less efficient.

All of the formulations were clear solutions which remained stable (by eye) for several days (>7 days).

It was observed that the API contributes to the formulation volume. A typical formulation in this study has a volume of 10.6-10.7 mL (API concentration 93-94 mg/mL).

Example 3—Infusion Solution Studies

The solubility of the NUC-1031 formulations in infusion solutions was investigated.
In the clinic it is intended to solubilise 2 g of API in 500 mL of infusion solution (4 mg/mL). The formulations described above were diluted to generate an infusion solution with a slightly higher API concentration (4.6-4.7 mg/mL) to represent a worst case scenario. The results are shown in Table 4.

TABLE 4

Solubility of NUC-1031 Formulations in Infusion Solutions
(p = precipitate; c = clear solution)

| Formulation | Infusion Solution | T = 0 hours | T = 2 hours | T = 4.5 hours | T = 7 hours | T = 24 hours |
|---|---|---|---|---|---|---|
| A | 0.45% saline | c | c | c | c | p |
| B | WFI | c | c | p | p | p |
| C | 0.45% saline | c | c | c | p | p |
| D | WFI | c | c | p | p | p |
| E | 0.45% saline | c | c | c | c | p |
| F | WFI | c | c | c | c | c |
| G | WFI | p | n/a | n/a | n/a | n/a |
| H | WFI | p | n/a | n/a | n/a | n/a |
| 1 | WFI | p | n/a | n/a | n/a | n/a |

Formulations B and F were selected for infusion bag studies.

Example 4—Infusion Bad Studies

Formulations B and F (5 mL of each) were injected into 100 mL WFI Baxter Viaflo® bags. Viaflo® bags are manufactured from a PVC free plastic. This eliminates the risk of leaching toxic phthalate compounds.

TABLE 5

Solubility of Formulations B and F in WFI Infusion Bags
(p = precipitate; c = clear solution)

| Formulation | Infusion Solution | T = 0 | T = 2 hours | T = 24 hours |
|---|---|---|---|---|
| Formulation B:<br>API - 1 g, DMA 4 mL,<br>Kolliphor ® EL - 6 mL | WFI | c | c | P |
| Formulation F:<br>API - 1 g, DMA 4 mL,<br>Kolliphor ® HS15-6 mL | WFI | c | c | P |

The above results show that formulations comprising DMA can be generated which, upon dilution with an aqueous vehicle, are capable of remaining stable for long enough to be administered to a patient. The formulations can be diluted until the DMA is a relatively minor component (1-2%), with the majority of the remainder of the solvent being water without gemcitabine-[phenyl-benzoxy-L-alaninyl)]-phosphate precipitating out of solution.

Example 5—Further Formulation Stability Studies

A range of further formulations of the (S)-isomer of gemcitabine-[phenyl-benzoxy-L-alaninyl)]-phosphate were prepared and investigated (Table 6).

TABLE 6

Further (S)-Isomer formulations

| Formulation | Target API Concentration (mg/mL) | API Weight* (g) | Formulation Volume (mL) | Excipients |
|---|---|---|---|---|
| J | 75 | 1.90 | 25 | 30% DMA,<br>70% Kolliphor ® ELP |
| K | 75 | 1.90 | 25 | 40% DMA,<br>60% Kolliphor ® ELP |
| L | 75 | 1.89 | 25 | 50% DMA,<br>50% Kolliphor ® ELP |
| M | 75 | 1.89 | 25 | 50% DMA,<br>50% Tween ® 80 |
| N | 100 | 2.53 | 25 | 30% DMA,<br>70% Kolliphor ® ELP |
| O | 100 | 2.54 | 25 | 40% DMA,<br>60% Kolliphor ® ELP |
| P | 100 | 2.54 | 25 | 50% DMA,<br>50% Kolliphor ® ELP |
| Q | 100 | 2.53 | 25 | 50% DMA,<br>50% Tween ® 80 |

*The actual AP weight factored in the potency 99.1% of the API

For each formulation the API was initially solubilised in DMA and then made up to volume in the volumetric flask with either Kolliphor® ELP or Tween® 80. The Kolliphor® ELP was melted by applying the minimum amount of heat required to achieve melting (50° C. oven, 10 minutes).

Filtration and Filling

The formulations were filtered manually through a syringe filter into 2 mL clear glass vials.

The formulations afforded a back pressure during filtration that made it physically difficult to pass the solution through a given filter and which contributed to sample loss. The greater the concentration of Kolliphor® ELP in the formulation the greater the back pressure experienced during filtration was.

The head space of the filled vials was flushed with nitrogen prior to sealing with a 13 mm West stopper and crimping with an aluminium overseal.

All of the vials were stored at 2-8° C. for 3 days prior to T=0 testing and putting into stability. No precipitate formation or gelling was observed in any of the vials.

Stability

For each formulation four vials were assessed for stability at 25° C. and four vials at 2-8° C.

Appearance—Batches 1-3 and 5-7 conformed to the description "clear colourless solution, free from visible particulates" at T=0 and 1 month at all storage conditions. Batches 4 and 8 conformed to the description "clear yellow solution, free from visible particulates" at T=0 and 1 month at all storage conditions.

Assay and Related Substances—Samples were analysed using the assay and related substances method ADP173 vs. 04 for NUC-1031. For the 100 mg/mL samples 200 μl was transferred to a 20 mL volumetric flask using positive displacement pipette and diluted to volume with diluent. For the 75 mg/mL samples 250 μl was transferred to a 20 mL volumetric flask using positive displacement pipette and diluted to volume with diluent.

TABLE 7

Assay 2-8° C.

| Formulation | Assay (mg/mL) T = 0 | Assay (mg/mL) 2-8° C. T = 1 m |
|---|---|---|
| J | 77.43 | 73.96 |
| K | 78.56 | 74.82 |
| L | 75.59 | 75.90 |
| M | 74.21 | 71.73 |
| N | 108.27 | 101.05 |
| O | 95.09 | 97.97 |
| P | 96.48 | 95.75 |
| Q | 94.95 | 73.90 |

TABLE 8

Assay 25° C./60% relative humidity

| Formulation | Assay (mg/mL) T = 0 | Assay (mg/mL) 25° C./60% RH T = 1 m |
|---|---|---|
| J | 77.43 | 73.90 |
| K | 78.56 | 74.74 |
| L | 75.59 | 75.94 |
| M | 74.21 | 64.80 |
| N | 108.27 | 103.76 |
| O | 95.09 | 98.51 |
| P | 96.48 | 97.70 |
| Q | 94.95 | 89.05 |

The formulations were then diluted in 0.45% saline and the stability was evaluated as indicated in Table 9.

TABLE 9

Stability of formulations in 0.45% saline

| Formulation | Excipients | API concentration in 0.45% saline (mg/mL) | pH | Osmolality (mOsm/kg) | Observation T = 6 hours | Observation T = 24 hours |
|---|---|---|---|---|---|---|
| J | 30% DMA, 70% Kolliphor ® ELP | 3 | 6.2 | 281 | Clear solution | Clear solution |
| K | 40% DMA, 60% Kolliphor ® ELP | 3 | 6.3 | 316 | Clear solution | Clear solution |
| L | 50% DMA, 50% Kolliphor ® ELP | 3 | 6.5 | 371 | Clear solution | Clear solution |
| M | 50% DMA, 50% Tween ® 80 | 3 | 7.1 | 377 | Clear solution | Clear solution |
| N | 30% DMA, 70% Kolliphor ® ELP | 5 | 6.3 | 292 | Clear solution | Precipitate - small amount |
| O | 40% DMA, 60% Kolliphor ® ELP | 5 | 6.3 | 458 | Clear solution | Precipitate - small amount |
| P | 50% DMA, 50% Kolliphor ® ELP | 5 | 6.3 | 437 | Clear solution | Precipitate - large amount |
| Q | 50% DMA, 50% Tween ® 80 | 5 | 7.0 | 471 | Clear solution | Solid gel |

The results indicate that the 75 mg/mL formulations (J-M) diluted to 3 mg/mL in 0.45% saline are physically stable for 24 hours. The 100 mg/mL formulations (N-Q) diluted to 5 mg/mL in 0.45% saline are physically stable up to 6 hours. Formulations L and O were evaluated on a different day by a different operator and the same results were obtained.

Infusion Solution Evaluation

The long term stability of the formulations were evaluated by diluting with 0.45% saline after the formulations had been stored for 1 month as indicated in Table 10.

TABLE 10

Formulations in 0.45% saline T = 1 month

| Formulation | Sample | Excipients | API concentration in 0.45% saline (mg/mL) | Observation T = 24 hours |
|---|---|---|---|---|
| J | T = 1 month 2-8° C. | 30% DMA, 70% Kolliphor ® ELP | 3 | Clear solution |
| J | T = 1 month 25° C. | 30% DMA, 70% Kolliphor ® ELP | 3 | Clear solution |
| K | T = 1 month 2-8° C. | 40% DMA, 60% Kolliphor ® ELP | 3 | Clear solution |
| K | T = 1 month 25° C. | 40% DMA, 60% Kolliphor ® ELP | 3 | Clear solution |
| L | T = 1 month 2-8° C. | 50% DMA, 50% Kolliphor ELP | 3 | Clear solution |
| L | T = 1 month 25° C. | 50% DMA, 50% Kolliphor ® ELP | 3 | Clear solution |
| M | T = 1 month 2-8° C. | 50% DMA, 50% Tween ® 80 | 3 | Clear solution |
| M | T = 1 month 25° C. | 50% DMA, 50% Tween ® 80 | 3 | Clear solution |
| N | T = 1 month 2-8° C. | 30% DMA, 70% Kolliphor ® ELP | 3 | Clear solution |
| N | T = 1 month 25° C. | 30% DMA, 70% Kolliphor ® ELP | 3 | Clear solution |
| O | T = 1 month 2-8° C. | 40% DMA, 70% Kolliphor ® ELP | 3 | Clear solution |
| O | T = 1 month 25° C. | 40% DMA, 60% Kolliphor ® ELP | 3 | Clear solution |
| P | T = 1 month 2-8° C. | 50% DMA, 50% Kolliphor ® ELP | 3 | Clear solution |
| P | T = 1 month 25° C. | 50% DMA, 50% Kolliphor ® ELP | 3 | Clear solution |
| Q | T = 1 month 2-8° C. | 50% DMA, 50% Tween ® 80 | 3 | Clear solution |
| Q | T = 1 month 25° C. | 50% DMA, 50% Tween ® 80 | 3 | Clear solution [00138] |

The results indicate that the 75 mg/mL formulations (J-M) and the 100 mg/mL formulations (N-Q) which have been stored for 1 month and then diluted to 3 mg/mL in 0.45% saline are physically stable after 24 hours.

The formulations that had been stored at 25° C. (for 2 months) and that contained Kolliphor ELP™ were evaluated in filtered 0.45% saline at a number of concentrations as indicated in Table 11.

TABLE 11

NUC-1031 formulations in 0.45% saline, T = 2 months, 25° C.

| Formulation | Composition | API concentration in 0.45% saline (mg/mL) | Observation T = 19 hours |
|---|---|---|---|
| J | 75 mg/mL API, 30% DMA, 70% Kolliphor ® ELP | 3 | Clear solution |
|  |  | 3.5 | Clear solution |
|  |  | 4 | Clear solution |
|  |  | 4.5 | Clear solution |
| K | 75 mg/mL, 40% DMA, 60% Kolliphor ® ELP | 3 | Clear solution |
|  |  | 3.5 | Clear solution |
|  |  | 4 | Clear solution |
|  |  | 4.5 | Clear solution |
| L | 75 mg/mL API, 50% DMA, 50% Kolliphor ® ELP | 3 | Clear solution |
|  |  | 3.5 | Clear solution |
|  |  | 4 | Clear solution |
|  |  | 4.5 | Clear solution |

TABLE 11-continued

NUC-1031 formulations in 0.45% saline, T = 2 months, 25° C.

| Formulation | Composition | API concentration in 0.45% saline (mg/mL) | Observation T = 19 hours |
|---|---|---|---|
| N | 100 mg/mL API, 30% DMA, 70% Kolliphor ® ELP | 3 | Clear solution |
| | | 3.5 | Clear solution |
| | | 4 | Clear solution |
| | | 4.5 | Clear solution |
| O | 100 mg/mL API, 40% DMA, 60% Kolliphor ® ELP | 3 | Clear solution |
| | | 3.5 | Clear solution |
| | | 4 | Clear solution |
| | | 4.5 | Clear solution |
| P | 100 mg/mL API, 50% DMA, 50% Kolliphor ® ELP | 3 | Clear solution |
| | | 3.5 | Clear solution |
| | | 4 | Clear solution |
| | | 4.5 | Clear solution |

The results indicate that the formulations diluted in 0.45% saline are physically stable up to a concentration of 4.5 mg/mL.

Example 7—Combinations of Solubilizers

Samples were prepared in which a combination of solubilizers was present.

First a 250 mg/mL solution of the S-epimer in DMA was prepared by dissolving the S-epimer in DMA. This was then diluted to a 100 mg/mL solution by addition of the desired combination of solubilizers, according to Table 12.

| Formulation No | DMA % | Kolliphor ® ELP % | Kolliphor ® HS15 % | Tween ® 80% |
|---|---|---|---|---|
| 1 | 40 | | 30 | 30 |
| 2 | 40 | | 20 | 40 |
| 3 | 40 | | 40 | 20 |
| 4 | 40 | 30 | | 30 |
| 5 | 40 | 20 | | 40 |
| 6 | 40 | 40 | | 20 |
| 7 | 40 | 30 | 30 | |
| 8 | 40 | 20 | 40 | |
| 9 | 40 | 40 | 20 | |
| 10 | 40 | 10 | 20 | 30 |
| 11 | 40 | 10 | 30 | 20 |
| 12 | 40 | 20 | 10 | 30 |
| 13 | 40 | 20 | 30 | 10 |
| 14 | 40 | 30 | 20 | 10 |
| 15 | 40 | 30 | 10 | 20 |
| 16 | 40 | 20 | 20 | 20 |

The formulations were each diluted in 0.45% saline (pH 5.9) to provide solutions that were 4 mg/mL, 6 mg/mL, 8 mg/mL and 10 mg/mL. The appearance of the solution was checked after stirring and after 3 hours, 6 hours and 24 hours of storage at ambient temperature. All solutions, including those at 10 mg/mL remained clear colourless solutions after 24 hours. The 10 mg/mL solution of formulation 3 did however show some cloudiness and particulate formation after 26 hours. HPLC analysis of the other 10 mg/mL solutions showed that the concentration of the active in solution and the purity of the active remained at the expected levels.

Thus, the use of combinations of more than one solubilizer can allow stable solutions of NUC-1031 to be formed at higher concentrations.

Example 8

A preferred formulation system for formulating NUC-1031 is as follows:

A 250 mg/mL solution of NUC-1031 (the S-epimer, the R epimer or a mixture thereof) is formed in an 80:20 (by volume) mixture of DMA and 0.9% saline. This system is sufficiently stable for long term storage and transport of NUC-1031.

This formulation can be administered to patients intravenously via a central line (e.g. a Hickman line, PICC line, Portacath). The intravenous administration apparatus will typically be flushed with an 80:20 (by volume) mixture of DMA and 0.9% saline both before and after administration of the formulation comprising NUC-1031. This helps mitigate the risk of any potential precipitation of NUC-1031 in the intravenous administration apparatus on contact with the saline flush.

Alternatively, where intravenous administration into a peripheral vein is the preferred method of administration this first formulation is then diluted to 100 mg/mL with a 40%:40%:20% mixture of DMA:Tween® 80:Kolliphor® ELP (eg 6.9 mL of 250 mg/ml NUC-1031 in 80:20 DMA: 0.9% saline is added to 10.35 mL of the DMA:Tween®80: Kolliphor® ELP diluent). The resultant (second) formulation has been shown to be stable for up to 5 days for both the S-epimer and for a mixture of the R and S epimers.

The final administration formulation is then prepared by diluting this second formulation to the desired concentration with saline. Solutions of a mixture of the R and S epimers at 4, 8 and 10 mg/mL have been shown to be stable (both to precipitation of NUC-1031 and to degradation of NUC-1031) for 48 hours after dilution of this formulation in both 0.45% and 0.9% saline at a range of pHs (4.5, 6.0 and 7.0), providing the mixtures were not stirred. The osmolarity of all of these solutions has also been shown to be acceptable for peripheral administration.

The invention claimed is:

1. A pharmaceutical formulation comprising:
   from 10% to 60% by volume DMA;
   from 10% to 80% by volume solubilizer or solubilizers;
   from 1% to 15% by volume aqueous vehicle; and
   from 50 mg to 150 mg per mL gemcitabine-[phenyl-(benzoxy-L-alaninyl)]-phosphate,
   wherein each solubilizer is a non-ionic surfactant or a mixture thereof; and
   wherein the aqueous vehicle is selected from saline, glucose solution and water for infusion (WFI).

2. The pharmaceutical formulation according to claim 1, wherein the aqueous vehicle is saline.

3. The pharmaceutical formulation according to claim 1, wherein the aqueous vehicle is WFI.

4. The pharmaceutical formulation according to claim 1, wherein each solubilizer is a polyethoxylated fatty acid or a mixture thereof.

5. The pharmaceutical formulation according to claim 1, wherein each solubilizer is a polyoxyl castor oil or a mixture thereof.

6. The pharmaceutical formulation according to claim 1, wherein gemcitabine-[phenyl-(benzoxy-L-alaninyl)]-phosphate is in the form of the (S)-phosphate epimer with a diastereoisomeric purity of greater than 95%.

7. The pharmaceutical formulation according to claim 1 for dilution with an aqueous vehicle to form a formulation for intravenous administration.

8. A method of preparing a pharmaceutical formulation according to claim 1, the method comprising:
   diluting a first formulation with a second formulation;
   wherein the first formulation comprises:
      from 200 mg to 300 mg per mL gemcitabine-[phenyl-(benzoxy-L-alaninyl)]-phosphate;
      from 70% to 90% by volume dimethyl acetamide (DMA); and
      from 10% to 30% by volume aqueous vehicle; and
   the second formulation comprises:
      from 20% to 70% by volume DMA;
      from 10% to 60% by volume a first solubilizer; and
      from 10% to 60% by volume a second solubilizer,
   wherein each solubilizer is a non-ionic surfactant or a mixture thereof; and
   wherein the aqueous vehicle is selected from saline, glucose solution and water for infusion (WFI).

9. The method according to claim 8, wherein gemcitabine-[phenyl-(benzoxy-L-alaninyl)]-phosphate is in the form of the (S)-phosphate epimer with a diastereoisomeric purity of greater than 95%.

10. A method of treating cancer, the method comprising:
    diluting a solution comprising:
       from 10% to 60% by volume DMA;
       from 30% to 80% by volume solubilizer or solubilizers;
       from 1% to 15% by volume aqueous vehicle; and
       from 50 mg to 150 mg per mL gemcitabine-[phenyl-(benzoxy-L-alaninyl)]-phosphate,
    with an aqueous vehicle to provide a formulation for infusion or injection; and
    administering the formulation for infusion or injection to the subject by infusion or injection,
    wherein each solubilizer is a non-ionic surfactant or a mixture thereof; and
    wherein the aqueous vehicle is selected from saline, glucose solution and water for infusion (WFI).

11. The method according to claim 10, wherein gemcitabine-[phenyl-(benzoxy-L-alaninyl)]-phosphate is in the form of the (S)-phosphate epimer with a diastereoisomeric purity of greater than 95%.

* * * * *